United States Patent [19]

Warriner

[11] Patent Number: Plant 6,010

[45] Date of Patent: Sep. 15, 1987

[54] ROSE PLANT JACSIL

[75] Inventor: William A. Warriner, Tustin, Calif.

[73] Assignee: Jackson & Perkins Company, Medford, Oreg.

[21] Appl. No.: 792,908

[22] Filed: Oct. 30, 1985

[51] Int. Cl.[4] ..... A01H 5/00

[52] U.S. Cl. ..... Plt./22

[58] Field of Search ..... Plt./22

*Primary Examiner*—James R. Feyrer

*Attorney, Agent, or Firm*—Manford R. Haxton

[57] ABSTRACT

A floribunda rose variety having unusual pale lavender color (near silver) coupled with attractive dark green foliage, few prickles, high cut flower production and a vigorous upright habit of growth.

1 Drawing Figure

This present invention relates to a new and distinct variety of rose plant of the floribunda class which was originated by crossing an unnamed variety with the variety Angel Face, U.S. Plant Pat. No. 2,792.

The primary objective of this breeding was to produce a new rose variety of a lavender color suitable for use as a greenhouse cut flower. This objective was substantially achieved along with other desirable improvements as evidenced by the following unique combination of characteristics which are outstanding in the new variety and which distinguish it from its parents as well as from all other varieties of which I am aware:

1. Vigorous, upright and productive plant;
2. Slight, pleasing fragrance;
3. An attractive pale lavender color (75B to C) in the bud opening to a near silver color (69B to D);
4. Glossy dark green foliage; and
5. Few and large prickles.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated Parentage:

*Seed parent.*—Unnamed variety.

*Pollen parent.*—Angel Face, U.S. Plant Pat. No. 2,792.

Classification:

*Botanical.*—Rosa hybrid.

*Commercial.*—Floribunda.

FLOWER

Observations made from specimens grown in a greenhouse at Irvine, Calif. in July.

Blooming habit: Continuous.

Bud:

*Size.*—1 to 1¼" when petals start to unfurl.

*Form.*—Long, blunt top.

*Color.*—When sepals first divide, Purple Group 75B to C; when half blown, upper side of petals 69B to 69D; lower side of petals 69B to 69D.

*Sepals.*—Color: 138B. Three appendaged sepals normally appendaged. Two unappendaged sepals hairy edge.

*Receptacle.*—Color: Green 138B. Shape: Funnel. Size: Medium, broad. Surface: Slightly hairy.

*Peduncle.*—Length: Medium. Surface: Prickly, glandular. Color: Medium green. Strength: Stiff, erect.

Open bloom:

*Size.*—Medium. Average open size 2½-3".

*Borne.*—Singly, several together.

*Stems.*—Long, strong.

*Form.*—When first open, high center. Permanence: Flattens.

*Petalage.*—Number of petals under normal conditions: 30-35.

*Color.*—Center of flower: Upper side of petals, 69B to 69D; reverse side of petals, 69C to D. Base of petals, Yellow Group 2D, small area at point of attachment. Major color: 69B to 69D.

*Variegations.*—None.

*Discoloration.*—General tonality at end of third day: Fades slightly.

*Fragrance.*—Slight.

Petals:

*Texture.*—Thick.

*Shape.*—Round.

*Form.*—Tips slightly recurved.

*Arrangement.*—Imbricated. Petaloids in center, few.

*Persistence.*—Drop off cleanly.

*Lastingness.*—On the plant, long. As cut flower, fair.

Reproductive parts:

*Anthers.*—Large, many. Color: Yellow. Arrangement: Regular around styles.

*Filaments.*—Color: White.

*Pollen.*—Gold Yellow.

*Styles.*—Color: White.

*Stigmas.*—Color: Yellow.

PLANT

Form: Bush.

Growth: Vigorous, upright.

Foliage: Number of leaflets on normal mid-stem leaves: 5–7.

*Size.*—Large.

*Quantity.*—Normal.

*Color.*—New foliage: Greyed Purple 187B to D. Old foliage: Medium Green.

Leaflets:

*Shape.*—Elliptic.

*Texture.*—Leathery, glossy.

*Edge.*—Serrated.

*Serration.*—Single, small.

*Petiole.*—Rachis: Color: Green. Underside: Smooth, with prickles.

*Stipules.*—Medium, bearded.

*Disease resistance.*—Susceptible to mildew, under normal growing conditions at Irvine, Calif.

Wood:

*New wood.*—Color: Reddish. Bark: Smooth.

*Old wood.*—Color: Green. Bark: Smooth.

Prickles:

*Quantity.*—On main canes from base: Few. On laterals from main canes: Few.

*Form* .—Long, hooked downward.

*Color when young.*—Red.

Small prickles:

*Quantity.*—On main stalks, none. On laterals, none.

I claim:

1. A new and distinct variety of rose plant of the floribunda class, substantially as herein shown and described, characterized particularly as to novelty by the unique combination of its unusual pale lavender color (near silver) coupled with attractive dark green foliage, few prickles, high cut flower production and a vigorous upright habit of growth.

* * * * *

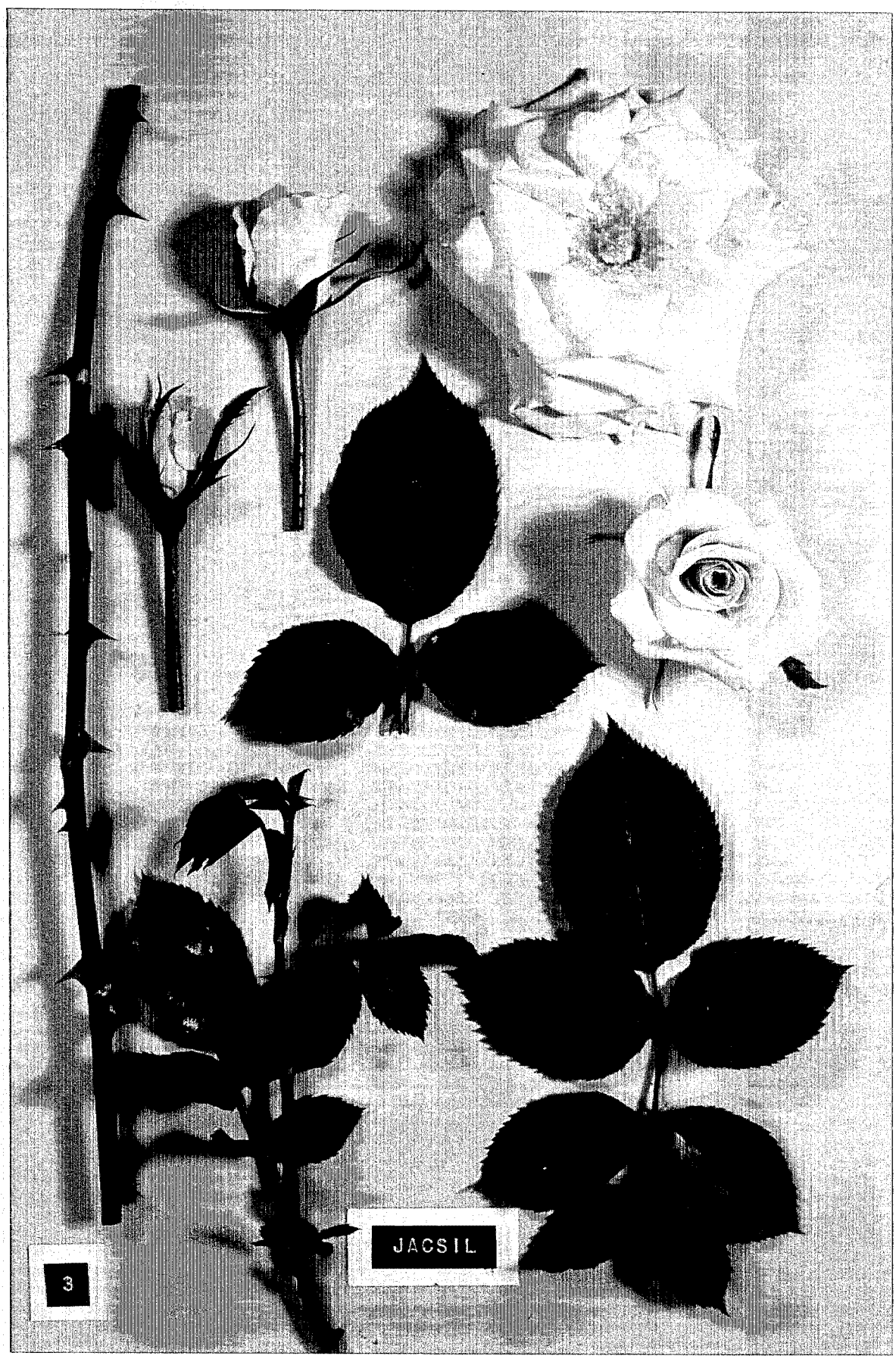
JACSIL
3